United States Patent [19]

McMullen

[11] 4,004,978

[45] Jan. 25, 1977

[54] MICROBIOLOGICAL REDUCTION OF ZEARALENONE AND RELATED COMPOUNDS

[75] Inventor: James Robert McMullen, Terre Haute, Ind.

[73] Assignee: IMC Chemical Group, Inc., Terre Haute, Ind.

[22] Filed: Sept. 19, 1975

[21] Appl. No.: 615,044

[52] U.S. Cl. .............................................. 195/51 R
[51] Int. Cl.² ........................................ C12D 13/00
[58] Field of Search .................................. 195/51 R

[56] References Cited

UNITED STATES PATENTS

| | | |
|---|---|---|
| 2,753,290 | 7/1956 | Fried et al. ........................ 195/51 |
| 2,877,161 | 3/1959 | Sebek et al. ........................ 195/51 |
| 3,386,890 | 6/1968 | Vezina et al. ...................... 195/51 |
| 3,580,811 | 5/1971 | Hidy ................................ 195/36 R |
| 3,793,148 | 2/1974 | Lanzilotta ........................ 195/51 R |

*Primary Examiner*—Alvin E. Tanenholtz
*Attorney, Agent, or Firm*—Morton, Bernard, Brown, Roberts & Sutherland

[57] ABSTRACT

A method for microbiologically reducing zearalenone and related compounds comprising cultivating a ketone-reducing microorganism in a nutrient medium and exposing the compound being reduced to the enzyme action of said microorganism.

17 Claims, No Drawings

MICROBIOLOGICAL REDUCTION OF ZEARALENONE AND RELATED COMPOUNDS

The present invention relates to a method for microbiologically reducing zearalenone and related compounds. More particularly, the present invention relates to a method for microbiologically reducing the ketone group of zearalenone and related compounds (hereinafter sometimes called keto-compounds) to a hydroxyl group. The nomenclature used herein conforms to that described in an article in *Tetrahedron Letters*, Pergamon Press, Ltd., No. 27, pp. 3109–3114 (1966).

The zearalenone compounds which may be reduced by the method of this invention are represented by the formula

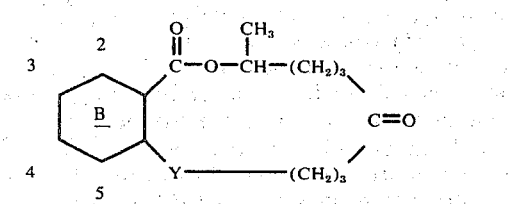

wherein B is a six-carbon ring which may be saturated, unsaturated, or aromatic and may be substituted with one or more members selected from the group consisting of hydrogen; hydroxy; lower alkoxy of from 1 to about 6 carbon atoms, such as methoxy, ethoxy, propoxy, pentoxy and the like; lower alkanoyloxy of from 1 to about 6 carbon atoms, such as formyloxy, acetoxy, butyroyloxy, and the like; monocyclic aryloxy of about 6 to 8 carbon atoms, such as phenyloxy, tolyloxy, etc.; and monocyclic aralkyloxy, that is, an alkoxy group having an aryl substituent thereon, wherein the alkoxy portion has 1 to about 5 carbon atoms and the aryl portion has about 6 to 8 carbon atoms such as benzyloxy, tolyl methoxy and the like; and Y is selected from the group consisting of —CH$_2$—CH$_2$— and —CH=CH—. The compounds are reduced to hydroxy-compounds of the formula

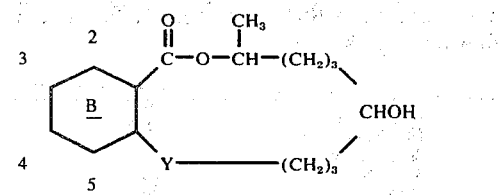

wherein the substituents have the same meanings as described above.

This invention is particularly advantageous as a method for reducing keto-compounds of the formula

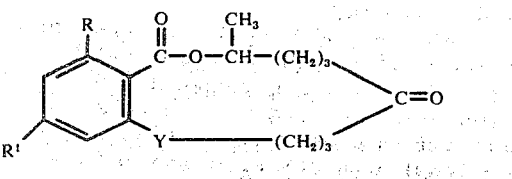

to hydroxy-compounds of the formula

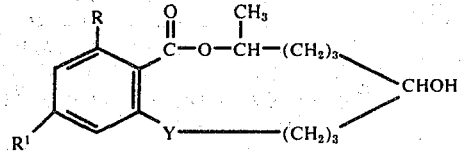

wherein R and R$^1$ may be the same or different and each is selected from the group consisting of hydrogen, hydroxy, and —OR$^2$, wherein R$^2$ is selected from the group consisting of lower alkyl of from 1 to about 6 carbon atoms, monocyclic aryl of about 6 to 8 carbon atoms, and monocyclic aralkyl wherein the alkyl portion has 1 to about 5 carbon atoms and the aryl portion has about 6 to 8 carbon atoms; and Y is selected from the group consisting of —CH$_2$—CH$_2$— and —CH=CH—.

Exemplary of the method of this invention are the reductions of zearalenone to zearalenol (wherein B is an aromatic ring substituted in the 2 and 4 positions with hydroxyls, and Y is —CH=CH—), zearalanone to zearalanol (wherein B is an aromatic ring substituted in the 2 and 4 positions with hydroxyls, and Y is —CH$_2$—CH$_2$—), dideoxyzearalanone to dideoxyzearalanol (wherein B is an unsubstituted aromatic ring, and y is —CH$_2$—CH$_2$—), dimethyl zealenone to dimethylzearalenol (wherein B is an aromatic ring substituted in the 2 and 4 positions with methoxy groups, and Y is —CH=CH—), tetrahydrozearalanone to tetrahydrozearalanol (wherein B is a saturated ring substituted in the 2 and 4 positions with hydroxyls, and Y is —CH$_2$—CH$_2$—), etc.

The keto-compounds which may be reduced by the method of this invention may be prepared from zearalenone, which is represented by the following structural formula:

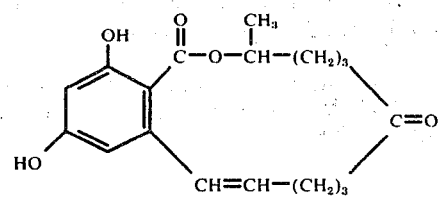

Zearalenone is a natural fermentation product which may be produced by cultivating a zearalenone-producing strain of the microorganism *Giberella zeae* on a suitable nutrient medium as described by Andrews, F. N., et al, U.S. Pat. No. 3,196,019, July 20, 1965, incorporated herein by reference. Preparations of keto-compounds in which B is a substituted aromatic ring are disclosed by Hodge, E. B., et al., U.S. Pat. No. 3,239,341, Mar. 8, 1966, incorporated herein by reference. Preparations of compounds in which B is an unsubstituted aromatic ring are disclosed by Wehrmeister, H. L., et al, U.S. pat. application Ser. No. 302,414, filed Oct. 31, 1972, now U.S. Pat. No. 3,887,583 which is incorporated herein by reference. Keto-compounds in which B is a saturated ring are described by Abbott, R. L., U.S. Pat. No. 3,373,037, which issued Mar. 12, 1968, incorporated herein by reference.

The hydroxy-compounds which are the products of the method of this invention exhibit estrogenic activity or aid in increasing the rate of growth of meat-producing animals, e.g. cattle, lamb, and swine. The compounds can be administered to animals by any suitable method including oral and parenteral administrations. For example, the compound can be blended with ordinary feed containing nutritional values in amounts sufficient to produce the desired rate of growth and can thus be fed directly to the animals, or the compound can be suspended in a suitable injection suspension medium such as peanut oil and injected parenterally. The amount of compound administered to an animal varies depending upon the animal, desired rate of growth, and the like.

The reduction of the ketone group of zearalenone and related compounds has heretofore been accomplished by chemical means. The reduction has been accomplished, for example, by catalytic reduction with hydrogen in the presence of Raney nickel. Hodge, E. B., et al., U.S. Pat. No. 3,239,345, Mar. 8, 1966, describes such a reduction. When the ketone group of naturally produced zearalenone, or a derivative thereof, is chemically reduced, the resulting hydroxy-compound has two asymmetric carbon atoms, one of which (at the 10' position) exists in only one isomeric configuration, and the other (at the 6' position) exists in either of two isomeric configurations. Thus, the hydroxy-compound exists in two diastereoisomeric forms. The two diastereoisomeric forms differ somewhat in physical properties, such as melting points, and in biological activity. The diastereoisomer having the higher melting point has generally been preferred, particularly in compounds used to increase the rate of growth in meat producing animals. Various reductive methods have been devised to enhance the concentration of this diastereoisomer in the reduction product, however, no known chemical reductive method yields only the desired form. Accordingly, there is a need for a method for stereospecifically reducing zearalenone and related compounds to hydroxy-compounds in which the hydroxyl group in the 6' position has the desired configuration.

In accordance with the invention, there has been discovered a method for reducing a keto-compound of the formula

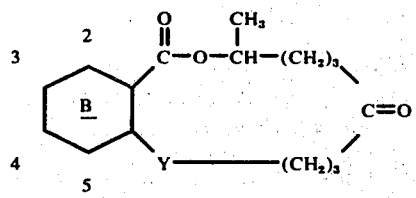

to a hydroxy-compound of the formula

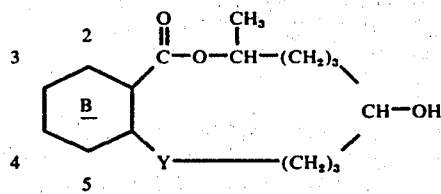

wherein B is a six-carbon ring which may be saturated, unsaturated, or aromatic and may be substituted with one or more members selected from the group consisting of hydrogen, hydroxy, lower alkoxy of from 1 to about 6 carbon atoms, lower alkanoyloxy of from 1 to about 6 carbon atoms, monocyclic aryloxy of about 6 to 8 carbon atoms, and monocyclic aralkyloxy wherein the alkoxy portion has from 1 to about 5 carbon atoms and the aryl portion has about 6 to 8 carbon atoms and Y is selected from the group consisting of —CH$_2$—CH$_2$— and —CH=CH—, which comprises cultivating a ketone-reducing, enzyme-producing microorganism in a nutrient fermentation medium and contacting the keto-compound with the ketone-reducing enzyme produced by the microorganism under ketone-reducing conditions to reduce the keto-compound to produce the hydroxy-compound.

The method of the present invention comprises subjecting a keto-compound to the enzyme action of a viable culture of a ketone-reducing, enzyme-producing microorganism. Any microorganism which produces an enzyme which reduces the ketone group of zearalenone and related keto-compounds to a hydroxyl group may be employed. Such microorganisms may be obtained from depositories such as the Northern Regional Research Laboratories, Peoria, Illinois or the American Type Culture Collection, Washington, D.C., or the microorganisms may be isolated from natural sources such as soil samples. Methods for isolating and storing such microorganisms, are generally known by skilled microbiologists. Specific microorganisms which have been found effective in reducing keto-compounds are *Penicillium frequentans*, ATCC 11080; *Aspergillus quadrilineatus*, ATCC 12067; *Penicillium rubrum*, ATCC 10520; *Syncephalastrum elegans*, ATCC 20471; *Chaetomium globosum*, ATCC 20470; *Candida lipolytica*, ATCC 8662; and *Rhodotorula rubra*, ATCC 4558. The ATCC numbers refer to the catalog numbers assigned to the microorganisms on deposit at the American Type Culture Collection. The preferred microorganism for the method of this invention is a yeast, *Rhodotorula rubra*.

The microorganism which is chosen for the reduction is advantageously grown and stored on a suitable agar slant culture. The composition of the medium used for the slant culture is not critical so long as it is sterile and contains adequate nutrients and growth factors to support the microorganism. A suitable slant medium has been found to be Bennett's Agar, which contains the following ingredients:

| Beef Extract | 1 g |
| NZ Amine A* | 2 g |
| Yeast Extract | 1 g |
| Glucose | 10 g |
| Agar | 20 g |
| H$_2$O | to one liter |

*pancreatic digest of casein

The reduction is carried out by growing the microorganism in a nutrient fermentation medium and exposing the keto-compound to the reductive enzyme action of the microorganism.

Suitable nutrient fermentation media are aqueous mixtures which contain assimilable sources of nitrogen and carbon, and growth-promoting amounts of growth factors such as minerals and vitamins. Examples of assimilable nitrogen sources are proteins, peptonized beef broth, urea, asparagine, ammonium salts such as ammonium nitrate and ammonium fumarate, glutamine, glycine, and pancreatic digest of casein. The preferred nitrogen source, either as the sole source, or used in conjunction with others, is a pancreatic digest of casein such as NZ Amine Type A purchased from Sheffield Chemical Division of National Dairy Products, Norwich, New York. The nitrogen source is present in the medium in growth-promoting amounts. Satisfactory concentrations of a pancreatic digest of casein, for example, range from about 0.5 grams per liter to about 100 grams per liter, preferably about 10 to 30 grams per liter of fermentation medium.

The assimilable carbon source is advantageously glucose, e.g. reagent grade glucose or Cerelose, a white, crystallized, refined glucose. Other suitable, but less preferred carbon sources are other carbohydrates which will not deleteriously effect the reduction of keto-compounds, such as xylose, fructose, sucrose, maltose, glycerol, sorbitol, and galactose. As an alternative to supplying actual glucose to the fermentation medium, a precursor thereof, such as starch, which under the conditions of the method, will be converted to glucose, can also be used. The assimilable carbon is added to the fermentation medium in growth-promoting amounts. Glucose is generally added to the medium at a concentration of from about 1 gram to about 200 grams per liter or more of fermentation medium, preferably from about 50 grams to about 60 grams per liter of fermentation medium.

Minerals such as magnesium, sodium, potassium, and iron salts of phosphates, chlorides, sulfates, etc. and other growth factors, such as vitamins, e.g. B. vitamins; coenzymes; and other organic substances are advantageously added to the medium. Important vitamins and various other growth factors, including certain minerals, are advantageously introduced into the medium via a yeast extract. The yeast extract is usually present in amounts of from about 0.1 gram per liter to about 10 grams per liter, preferably about 1 to 4 grams per liter of fermentation medium. If a pancreatic casein digest is employed as the nitrogen source, certain minerals and vitamins are also provided by it. A particularly preferred fermentation medium contains, in one liter, glucose (Cerelose), 55 grams; pancreatic casein digest (NZ Amine Type A), 20 grams; yeast extract, 2 grams; and distilled water, q.s.

Other non-deleterious ingredients such as antifoaming agents, e.g. silicone foam inhibitors, corn oil, lard oil, mineral oil, etc. may be added to the fermentation medium in the desired amounts.

A suitable size aliquot of the fermentation medium is transferred to a container such as an Erlenmeyer flask, which is then capped with a filter e.g. cotton, to prevent contaminating bacteria from entering and is preferably sterilized prior to inoculation, for instance by autoclaving or subjecting to steam at superatmospheric pressures. After sterilization, the medium is inoculated by transferring to it an inoculum containing a viable culture of the microorganism from, for instance, an agar slant or other source.

The keto-compound may be introduced into the fermentation medium prior to inoculation, or at any time during the growth of the microorganism, however, the preferred technique is to add the keto-compound after substantial growth has occurred. The medium is incubated at a temperature sufficient for optimal growth, for a time sufficient to provide a substantial cell concentration for the reduction. Incubation temperatures are generally from about 10° C to about 60° C, preferably about 20° C to 35° C. A substantial cell concentration is preferably achieved prior to the addition of the keto-compound. Such a cell concentration is generally obtained after from about 16 hours to about 30 hours preferably about 22 to 26 hours from the time of inoculation.

After a suitable growth has been obtained the keto-compound may be added to the fermentation medium. The keto-compound may be added in any convenient form, but preferably is added from a solution, e.g. an alcohol solution of the compound. The keto-compound is introduced into the fermentation medium at a concentration sufficiently high to provide optimal reduction efficiency, but not too high to cause significant amounts of unreacted ketocompound to remain in the medium. Concentrations of from about 0.001 mg/100 ml to about 200 mg/100 ml, preferably about 50–100 mg/100 ml of fermentation medium provide satisfactory results. The lower the concentration of the keto-compound, the more complete is the reduction; however, based on the cost of the medium, recovery, etc., optimum overall efficiency occurs at higher concentrations. The solubility of the keto-compound in the aqueous fermentation medium limits, to some extent, the maximum concentration at which the keto-compound can be reduced efficiently. Various means may be employed to increase the solubility of the keto-compound in the medium. Such means include the formation of a more soluble complex or salt of the compound, or controlling the pH of the medium. The preferred method of increasing the solubility of the keto-compound is by controlling the pH of the fermentation medium in a range of from about 6 to about 11.5, preferably about 7 to about 10.5. The "controlling" may or may not involve an actual pH adjustment, e.g. an increase of the pH of the medium. If, however, an upward adjustment of the pH is required, this may be accomplished by the addition of a suitable pH-increasing base such as sodium hydroxide or ethylenediamine to the fermentation medium in amounts sufficient to achieve the desired pH.

The keto-compound is exposed to the reducing action of the microorganism for a time sufficient to provide substantial reduction. Generally from about 3 hours to about 36 hours is adequate, about 20 to 28 hours being preferred.

The reductive microorganisms used in this method generally function either aerobically or anaerobically. It has been found, however, that optimum results are obtained when the growth stage, i.e. the period between inoculation and addition of the keto-compound, is conducted aerobically and the reduction stage, i.e. after addition of the keto-compound, is conducted anaerobically. This technique is advantageously accomplished by agitating the fermentation medium during the growth stage, for instance, by shaking or sparging with air, and sealing the vessel containing the fermentation from air during the reduction stage.

The reduction of the ketone group by the method of this invention occurs through the action of an enzyme or combination of enzymes produced intracellularly by the microorganism. For this reason, the efficiency of the reduction may be improved by increasing the effective concentration of the enzymes produced by the microorganism. Frequently, the concentration of the enzymes is increased by a factor of 1 to about 3 times prior to the introduction of the keto-compound. This effect may be accomplished by enhancing the cell concentration, for instance, by centrifuging a portion of the fermentation medium, and resuspending the concentrated cells in another portion of whole medium. This technique provides improved reduction efficiencies, for instance, by doubling the cell concentration, an approximate 20% increase in the percentage of keto-compound reduced may result. Another method of effectively increasing enzyme concentration is by disrupting the cells to free the enzymes, thus providing greater exposure of the keto-compound to the action of the enzymes. In this case, the disrupted cells may be removed and the cell-free enzyme solution may be used for the reduction.

After the reduction has been accomplished, the product may be recovered by any suitable method. A suitable recovery method comprises acidifying the fermentation medium to a pH of from about 1.5 to about 5 with a mineral acid, e.g. HCl or $H_2SO_4$; extracting the acidified fermentation medium with a suitable water-immiscible solvent in which the keto-compound is soluble such as chloroform or methylene chloride; and removing the water-immiscible solvent to leave a residue containing the reduction product. The product may be further purified, for instance, by recrystallization or distillation depending upon the particular product formed.

It is apparent, therefore, that a method has been discovered for stereospecifically reducing zearalenone and related keto-compounds to hydroxy-compounds by the action of a ketone-reducing microorganism. The invention is further illustrated by following examples which are not intended to limit the invention.

All of the microorganisms described in the following examples were stored on Bennett's Agar slant cultures.

EXAMPLE I

Several cultures from various sources were tested by the following procedure for their ability to reduce zearalenone. A fermentation medium having the following composition was prepared:

| | |
|---|---|
| Cerelose | 55 g |
| NZ Amine A | 20 g |
| Yeast Extract | 2 g |
| Distilled Water to 1 liter | |

The medium was dispensed in 100 ml quantities into 500 ml Erlenmeyer flasks. The flasks were capped with two milk filters and one sheet of Kraft paper (paper removed before inoculation). The flasks of medium were autoclaved at fifteen pounds steam pressure for fifteen minutes.

Flasks of the medium were routinely inoculated from slant cultures and incubated at 30° C on a rotary shaker. After suitable growth in the fermentation medium (usually 24 hours), one ml of an alcoholic solution of zearalenone (50 mg of zearalenone/ml of ethanol or methanol) was aseptically added. The flasks were incubated at 30° C for 72 hours on a slow shaker.

For detecting ability to reduce zearalenone, the whole cultures were adjusted to pH 2 with concentrated hydrochloric acid and shaken vigorously with 50–100 ml of chloroform. The resulting mixture was filtered through filter paper to remove cells or mycelium. The filtrate was poured into a separatory funnel and the phases were allowed to separate. The chloroform layer was drawn off into a flask and a portion was evaporated on a steam bath. The residue was dissolved in one ml of chloroform and spotted on silica gel thin-layer chromatography plates. The TLC plates were developed in chloroform:glacial acetic acid (90:10) or cyclohexane:ethyl acetate (2:1). The developed plates were air dried and viewed under short and long wave ultraviolet light. Zearalenone and zearalenol standards were spotted on the plates as markers. Reduction was indicated by a fluorescing and quenching spot with the $R_f$ of zearalenol. Some of the cultures which exhibited the ability to reduce zearalenone were identified to be *Penicillium frequentans*, *Aspergillus quadrilineatus*, *Penicillium rubrum*, *Syncephalastrum elegans*, *Chaetomium globosum*, *Candida lipolytica*, and *Rhodotorula rubra*.

EXAMPLE II

One hundred milliliters of fermentation medium prepared as described in Example I, was transferred to a 500 ml Erlenmeyer flask. The flask was capped with two milk filters and one sheet of Kraft paper (paper removed before inoculation). The flask was autoclaved at 15 lb. steam pressure for 15 minutes and cooled to about 30° C. The medium was inoculated with a culture of the yeast *Rhodotorula rubra* and incubated under vigorous agitation for 24 hours at 30° C. An alcoholic solution of zearalenone (1 ml, 50 mg zearalenone) was aseptically added, and the medium was further incubated for 72 hours without agitation. The medium was then shaken with 50 ml of methylene chloride and centrifuged. The lower, methylene chloride layer was withdrawn with a syringe and evaporated to dryness. The residue was redissolved in one ml of methylene chloride and spotted on a thin-layer chromatography plate. The thin-layer plate was developed in chloroform:glacial acetic acid (90:10). The zearalenone and zearalenol bands were scraped off the plate and separately eluted with methanol. Since the two compounds have approximately the same U.V. maxima, and extinction coefficients, the % conversion was calculated as follows:

$$\% \text{ conversion} = \frac{\text{absorbance of zearalenol}}{\text{absorbance of zearalenol} + \text{absorbance of zearalenone}}$$

The experiment resulted in about a 44% conversion of zearalenone to zearalenol.

EXAMPLE III

The experiment of Example II was repeated in all essential details except varying concentrations of zearalenone were reduced. The following table summarizes the results.

| Zearalenone Added mg/100 ml of medium | % Conversion of zearalenone to zearalenol |
|---|---|
| 6.25 | 78.9 |
| 12.5 | 84.7 |
| 25 | 83.2 |
| 75 | 24.4 |
| 100 | 17.1 |

EXAMPLE IV

The experiment of Example II was repeated in all essential details, except the pH of the fermentation medium was adjusted to 8.5 with an aqueous solution of ethylenediamine prior to addition of zearalenone. A 70% conversion was achieved.

EXAMPLE V

The experiment of Example II was repeated in all essential details except the pH of the fermentation medium was adjusted to 8.5 with an aqueous solution of sodium hydroxide prior to the addition of zearalenone. A 67% conversion was achieved.

EXAMPLE VI

Media containing various cell concentrations were prepared to determine the effect on reduction efficiency. Fermentation media were prepared, inoculated, and incubated for 24 hours at 30° C as described in Example II. Cell concentrations were reduced from the normal level by centrifuging portions of the cells out. Higher cell concentrations than normal were achieved by resuspending cells which were centrifuged out of media back into whole medium. The reduction stage of the fermentation was conducted as described in Example II. The results are summarized in the following table.

| Cell Concentration (% of normal concentration of whole medium) | % Conversion |
| --- | --- |
| 25% | 19.2 |
| 50% | 39.1 |
| 75% | 47.7 |
| 100% | 65.3 |
| 150% | 85.6 |
| 200% | 88.9 |

EXAMPLES VII-XII

A series of experiments is conducted in which keto-compounds of the structure

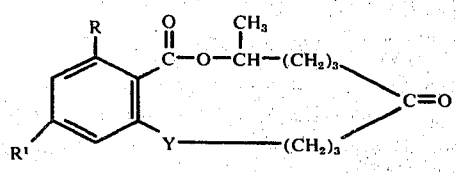

are reduced to hydroxy-compounds, wherein the substituents of the starting material of each particular example are shown in the following table. In each example, the procedure in Example II is repeated in all essential details with the exception that a different starting material is used. Each example results in satisfactory reduction of the keto-compound to a corresponding hydroxy-compound, having the following structure

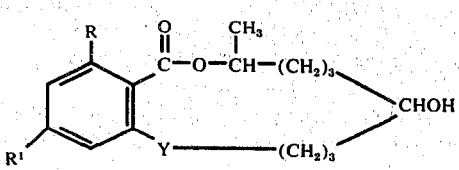

| Example | R | R¹ | Y |
| --- | --- | --- | --- |
| VII | —H | —H | —CH₂—CH₂— |
| VIII | —OH | —OH | —CH₂—CH₂— |
| IX | —OCH₃ | —OCH₃ | —CH=CH— |
| X | —O—φ* | —OH | —CH₂—CH₂— |
| XI | —OCH₂φ* | —OCH₂φ* | —CH=CH— |
| XII | —OCH₂CH₂CH₃ | —OCH₂CH₂CH₃ | —CH=CH— |

*φ indicates phenyl

I claim:
1. A method for reducing a keto-compound of the formula

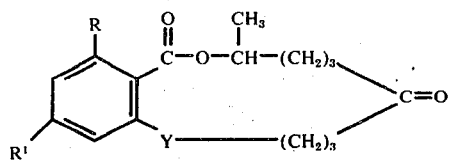

to a hydroxy-compound of the formula

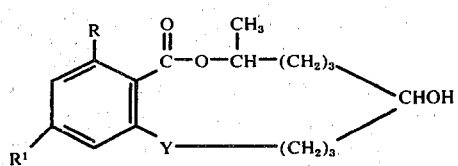

wherein R and R¹ may be the same or different and each is selected from the group consisting of hydrogen, hydroxy, and —OR², wherein R² is selected from the group consisting of lower alkyl of from 1 to about 6 carbon atoms, monocyclic aryl of about 6 to 8 carbon atoms, and monocyclic aralkyl, in which the alkyl portion has 1 to about 5 carbon atoms and the aryl portion has about 6 to 8 carbon atoms; and Y is selected from the group consisting of —CH₂—CH₂— and —CH=CH—, which comprises cultivating a ketone-reducing, enzyme-producing microorganism in a nutrient fermentation medium, said enzyme being capable of reducing the keto-group of said keto-compound, and contacting the keto-compound with the ketone-reducing enzyme produced by the microorganism to reduce the keto-compound to produce the hydroxy-compound.

2. The method of claim 1 wherein said microorganism is selected from the group consisting of *Penicillium frequentans*, *Aspergillus quadrilineatus*, *Penicillium rubrum*, *Syncephalastrum elegans*, *Chaetomium globosum*, *Candida lipolytica*, and *Rhodotorula rubra*.

3. The method of claim 1 wherein said microorganism is *Rhodotorula rubra*.

4. The method of claim 2 wherein said nutrient fermentation medium comprises assimilable sources of nitrogen, carbon, and growth factors.

5. The method of claim 2 wherein said nutrient fermentation medium comprises growth-promoting amounts of pancreatic digest of casein as an assimilable nitrogen source, glucose as an assimilable carbon source, and a yeast extract as a source of growth factors.

6. The method of claim 2 wherein said nutrient fermentation medium comprises from about 0.5 grams per liter to about 100 grams per liter of a pancreatic digest of casein; from about 1 gram per liter to about 200 grams per liter of glucose; and from about 0.1 gram per liter to about 10 grams per liter of a yeast extract, said cultivation is conducted at a temperature of from about 10° C to about 60° C, and the pH of said nutrient fermentation medium is controlled in a range of from about 6 to about 11.5.

7. The method of claim 2 wherein said nutrient fermentation medium comprises from about 10 grams per liter to about 30 grams per liter of a pancreatic digest of casein; from about 50 grams per liter to about 60 grams per liter of glucose; and from about 1 gram per liter to about 4 grams per liter of a yeast extract, said cultivation is conducted at a temperature of from about 20° C to about 35° C, and the pH of said nutrient fermentation medium is controlled in a range of from about 7 to about 10.5.

8. A method for reducing a keto-compound of the formula

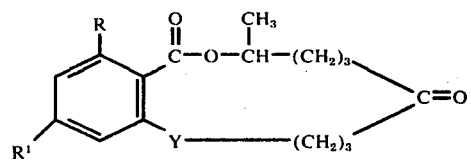

to a hydroxy-compound of the formula

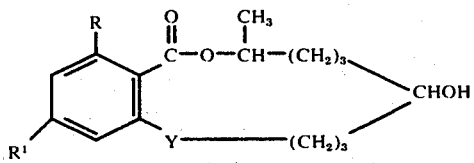

wherein R and $R^1$ may be the same or different and each is selected from the group consisting of hydrogen, hydroxy, and $-OR^2$, wherein $R^2$ is lower alkyl of from 1 to about 6 carbon atoms, monocyclic aryl of about 6 to 8 carbon atoms, and monocyclic aralkyl, in which the alkyl portion has 1 to about 5 carbon atoms and the aryl portion has about 6 to 8 carbon atoms; and Y is selected from the group consisting of $-CH_2-CH_2-$ and $-CH=CH-$, which comprises inoculating a nutrient fermentation medium with a ketone-reducing, enzyme-producing microorganism, said enzyme being capable of reducing the keto-group of said keto-compound; incubating said nutrient fermentation medium under aerobic conditions until substantial cell concentration is achieved; introducing the keto-compound into the nutrient fermentation medium; and incubating said nutrient fermentation medium under substantially anaerobic conditions until substantial reduction of the keto-compound to the hydroxy-compound is achieved.

9. The method of claim 8 wherein said microorganism is selected from the group consisting of *Penicillium frequentans, Aspergillus quadrilineatus, Penicillium rubrum, Syncephalastrum elegans, Chaetomium globosum, Candida lipolytica,* and *Rhodotorula rubra.*

10. The method of claim 8 wherein said microorganism is *Rhodotorula rubra.*

11. The method of claim 9 wherein said nutrient fermentation medium comprises assimilable sources of nitrogen, carbon, and growth factors.

12. The method of claim 9 wherein said nutrient fermentation medium comprises growth-promoting amounts of a pancreatic digest of casein as an assimilable nitrogen source, glucose as an assimilable carbon source, and a yeast extract as a source of growth factors.

13. The method of claim 9 wherein said nutrient fermentation medium comprises from about 0.5 gram per liter to about 100 grams per liter of a pancreatic digest of casein; from about 1 gram per liter to about 200 grams per liter of glucose; and from about 0.1 gram per liter to about 10 grams per liter of a yeast extract, said cultivation is conducted at a temperature of from about 10° C to about 60° C, and the pH of said nutrient fermentation medium is controlled in a range of from about 6 to about 11.5.

14. The method of claim 9 wherein said nutrient fermentation medium comprises from about 10 grams per liter to about 30 grams per liter of a pancreatic digest of casein; from about 50 grams per liter to about 60 grams per liter of glucose; and from about 1 gram per liter to about 4 grams per liter of a yeast extract, said cultivation is conducted at a temperature of from about 20° C to about 35° C, and the pH of said nutrient fermentation medium is controlled in a range of from about 7 to about 10.5.

15. The method of claim 9 further comprising concentrating the cells of the microorganism in the nutrient fermentation medium by a factor of 1 to about 3 times prior to the introduction oduction of the keto-compound.

16. The method of claim 15 wherein said concentrating is accomplished by centrifuging said nutrient fermentation medium.

17. A method for reducing a keto-compound of the formula

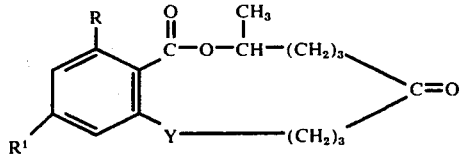

to a hydroxy-compound of the formula

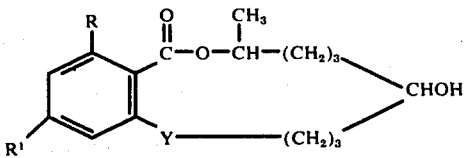

wherein R and $R^1$ may be the same or different and each is selected from the group consisting of hydrogen, hydroxy, and $-OR^2$, wherein $R^2$ is selected from the group consisting of lower alkyl of from 1 to about 6 carbon atoms, monocyclic aryl of about 6 to 8 carbon atoms, and monocyclic aralkyl, in which the alkyl portion has 1 to about 5 carbon atoms and the aryl portion has about 6 to 8 carbon atoms; and Y is selected from the group consisting of $-CH_2-CH_2-$ and $-CH=\lambda CH-$, which comprises contacting the keto-compound with an enzyme under ketone-reducing conditions to reduce the keto-compound to produce the hydroxy-compound, wherein said enzyme is capable of reducing the keto-group of said keto-compound and is produced by cultivating a microorganism capable of producing said enzyme in a nutrient fermentation medium.

* * * * *